(12) United States Patent
Verma

(10) Patent No.: US 8,454,680 B2
(45) Date of Patent: Jun. 4, 2013

(54) ENDOVASCULAR CONDUIT DEVICE WITH LOW PROFILE OCCLUSION MEMBERS

(75) Inventor: Sumit Verma, Pensacola, FL (US)

(73) Assignee: Atrial Systems, LLC, Pensacola, FL (US)

(*) Notice: Subject to any disclaimer, the term of this patent is extended or adjusted under 35 U.S.C. 154(b) by 97 days.

(21) Appl. No.: 12/896,092

(22) Filed: Oct. 1, 2010

(65) Prior Publication Data

US 2011/0082465 A1   Apr. 7, 2011

Related U.S. Application Data

(63) Continuation-in-part of application No. 12/500,832, filed on Jul. 10, 2009.

(60) Provisional application No. 61/249,026, filed on Oct. 6, 2009, provisional application No. 61/134,422, filed on Jul. 10, 2008.

(51) Int. Cl.
*A61F 2/06* (2006.01)
*A61F 11/00* (2006.01)

(52) U.S. Cl.
USPC ......... 623/1.25; 623/1.23; 623/1.24; 606/108

(58) Field of Classification Search
USPC ............... 623/1.23–1.25; 604/8–10; 606/129
See application file for complete search history.

(56) References Cited

U.S. PATENT DOCUMENTS

| | | | |
|---|---|---|---|
| 4,580,568 A | 4/1986 | Gianturco | |
| 5,171,261 A | 12/1992 | Noishiki | |
| 5,330,528 A | 7/1994 | Lazim | |
| 5,370,691 A | 12/1994 | Samson | |
| 5,649,978 A | 7/1997 | Samson | |
| 6,293,968 B1 | 9/2001 | Taheri | |
| 6,302,905 B1 | 10/2001 | Goldsteen | |
| 6,319,276 B1 | 11/2001 | Holman | |
| 6,395,019 B2* | 5/2002 | Chobotov | .................. 623/1.13 |
| 6,660,030 B2 | 12/2003 | Shaolian | |
| 6,776,604 B1 | 8/2004 | Chobotov | |
| 6,827,735 B2 | 12/2004 | Greenberg | |
| 7,147,660 B2 | 12/2006 | Chobotov | |
| 7,147,661 B2 | 12/2006 | Chobotov | |
| 7,150,758 B2 | 12/2006 | Kari | |
| 7,235,094 B2 | 6/2007 | Serino | |
| 2002/0151956 A1* | 10/2002 | Chobotov et al. | ............ 623/1.12 |
| 2006/0206197 A1 | 9/2006 | Morsi | |
| 2006/0206198 A1 | 9/2006 | Churchwell | |
| 2006/0206199 A1 | 9/2006 | Churchwell | |

* cited by examiner

*Primary Examiner* — Bruce E Snow
*Assistant Examiner* — Brian Dukert
(74) *Attorney, Agent, or Firm* — Mark S. Leonardo; Brown Rudnick LLP

(57) ABSTRACT

An endovascular conduit device and method for use during cardiac lead extraction and other vascular procedures is presented. The endovascular conduit device includes an outersheath, a conduit member, a lumen member, and an inflation member to control the flow of fluid within the conduit member. The endovascular conduit device may be positioned intravascularly as cardiac lead extraction or other procedures are performed. If necessary, as in the case of a vascular tear, the endovascular conduit device further includes expandable members that are activated to allow blood to be forced into the channel of the conduit member. Blood may then be contained and directed safely to bypass the area of vessel injury. In doing so, a catastrophic circulatory collapse or shock is prevented.

9 Claims, 15 Drawing Sheets

ENDOVASCULAR CONDUIT DEVICE WITH LOW PROFILE OCCLUSION MEMBERS

CROSS REFERENCE TO RELATED APPLICATION

This patent application claims priority to U.S. Provisional Application Ser. No. 61/249,026, filed in the U.S. Patent and Trademark Office on Oct. 6, 2009 and is a continuation-in-part application of U.S. application Ser. No. 12/500,832, filed in the U.S. Patent and Trademark Office on Jul. 10, 2009 that claims priority to U.S. Provisional Application Ser. No. 61/134,422, filed in the U.S. Patent and Trademark Office on Jul. 10, 2008, the entire contents of each are hereby incorporated by reference in their entirety.

BACKGROUND

1. Technical Field

The present disclosure generally relates to the field of catheters and devices that are inserted intravascularly for the purpose of medical treatment, and more particularly, to a device that increases safety during cardiac lead extraction procedures.

2. Description of the Related Art

Cardiac lead extraction is a procedure that is performed to properly manage patients with cardiac rhythm devices. Traditionally, the indications for removing implanted cardiac leads have resulted from infections caused by cardiac rhythm devices. More recently, these indications have expanded to include the removal of redundant leads, maintaining vascular access for upgrading devices, and the removal of recalled pacemaker and defibrillator leads. As a result, there is an increasing need for cardiac lead extraction procedures.

Cardiac lead extraction procedures are also required because cardiac leads are not lasting as long as desired due to increased patient longevity. In addition, as cardiac rhythm devices have increased in complexity, there is a need to upgrade such devices from single or dual chamber to biventricular pacers or implantable cardioverter-defibrillators (ICDs). This procedure involves adding additional leads through a patient's subclavian vein. The subclavian vein, however, can be occluded, thereby making cardiac lead placement impossible without removing the old leads and opening a channel. Lead extraction procedures may also be performed with mechanical and laser sheaths. The need for such sheaths is due to the formation of adhesions around a patient's veins over a period of time.

Referring now to FIG. 1, a perspective view of a heart and vessels with an implanted cardiac lead are presented. A cardiac lead 10 is seen to traverse from the left subclavian vein (not shown in Figure) into the left innominate vein 40, then into the right atrium 60, and through the tricuspid valve into the right ventricle 70. A lead extraction sheath 20 is advancing over cardiac lead 10 into the intravascular space. A cardiac lead tip or electrode is presented at a right ventricular apex 80 and adjacent to a left ventricle 90. One of the feared complications of a lead extraction procedure is a tear 52 at a superior vena cava 30 and a right atrial 60 junction that can result from traction and the use of laser sheaths or other energy sources. This complication results in the need for immediate open chest surgery to repair the tear 52. Due to sudden blood loss, hemodynamic collapse typically occurs and despite immediate open heart surgery, the patient may not survive. In anticipation of this feared complication, most physicians performing lead extraction prepare patients for possible open heart surgery. For example, it is typical for a cardiac surgeon to be available in the operating room as the cardiologist or cardiac electrophysiologist is performing the procedure in the event a vascular tear occurs.

Currently, there are no known methods to non-invasively prevent or treat a defect such as tear 52 at the superior vena cava 30 and right atrial 60 (SVC-RA) junction. Moreover, there are some cases involving patients that may be considered high risk for lead extractions. For example, certain patients demonstrate excessive scarring in the region of the SVC-RA junction but there is no known method to pre-determine this disposition. Specifically, patients demonstrating excessive scarring may be at higher risk for vessel injury and tear. It is generally accepted that cardiac leads that have been in place for many years pose an increase risk during extraction. It is also accepted that patients who have not had prior cardiac surgery can be at risk due to lack of adhesions around the heart that may otherwise limit or contain bleeding, if a tear were to occur. Other high risk categories include patients with multiple leads. Unfortunately, despite pre-operative risk assessment, complications still occur. The incidence of this particular complication is about three to four percent of all cases and in many cases the patient does not survive. The risk of death is generally reported to be about 0.4% of all cases.

Several techniques are presently utilized to prevent and treat vascular tears. For example, endovascular stenting is used to reopen narrowed vessels and to treat damaged vessels, such as in the case of endograft treatment for an aortic aneurysm. In another example, covered stents are used to patch or cover vascular tears using an endovascular approach. Although these stents work by direct apposition and contact with the vessel wall, the desired effect to treat damaged vessels is not achieved and external bleeding typically occurs as a result of poor stent to vessel wall contact. Similarly, in cases of lead extraction, if a covered stent is used, it may be deployed in different methods. For example, a stent may be passed over a wire and deployed in such a manner that the cardiac lead is external to the stent and sandwiched between the stent and vessel wall. In this case, there is poor stent to vessel contact and bleeding continues.

There is significant variability in instances in which leads are in contact with or scarred into the vessel wall. Due to these drawbacks, endovascular stenting may not be feasible. For example, stents are generally rigid and non-flexible. As a result, the complexity of anatomy involving the innominate vein, SVC and right atrium makes it difficult to achieve good stent apposition while maintaining blood flow to the heart. In addition, a user can no longer proceed with the lead extraction procedure because the lead is now trapped between the stent and vessel wall.

Another method is to position a covered endovascular stent through a wire passed through the lead extraction sheath. In this case, it is possible that a user may deploy the stent in such a manner that the cardiac lead is inside the stent and not outside. However, with this approach, difficulties arise because the stent may not be deployable as a result of adhesions, presence of multiple cardiac leads, or incomplete lead removal. Furthermore, in cases of right ventricular perforation, this method is ineffective.

Therefore, a need exists to allow cardiac lead extraction procedures to be performed with increased safety.

SUMMARY OF THE INVENTION

The invention relates to the field of catheters and devices that are inserted intravascularly for the purpose of medical treatment, and more particularly, to a device that increases safety during cardiac lead extraction procedures.

According to an aspect of the present disclosure, an endovascular conduit device is presented. The endovascular conduit device includes an outer-sheath having proximal and distal portions, a conduit member partially disposed within the distal portion of the outer-sheath, a lumen member disposed within the conduit member, and an inflation member disposed within one distal portion of the conduit member for use to control the flow of fluid within the conduit member.

According to another aspect of the present disclosure, an endovascular conduit device is presented. The endovascular conduit device includes an outer-sheath having proximal and distal portions, a conduit member partially disposed within the distal portion of the outer-sheath, and a lumen member disposed within the conduit member.

According to another aspect of the present disclosure, a method for utilizing an endovascular conduit device is presented. The method is comprised of the steps of inserting a conduit member, which has a proximal portion and one or more distal portions, and further includes at least one expandable member disposed within the proximal portion and the distal portions, into an outer-sheath having proximal and distal portions; advancing at least one guide-wire member into the proximal portion of a lumen member disposed within the conduit member through the distal portions of the conduit member; introducing an inflation means into the at least one expandable member through an inflation hub disposed to the proximal portion of the lumen member to create a seal and contain fluid within the conduit member; and actuating an inflation member disposed within one distal portion of the conduit member to control the flow of the fluid within the conduit member.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings as set forth below:

DETAILED DESCRIPTION OF THE EXEMPLARY EMBODIMENTS

The present disclosure generally relates to the field of catheters and devices that are inserted intravascularly for the purpose of medical treatment, and more particularly, to a device that increases safety during cardiac lead extraction procedures.

In the discussion that follows, the term "proximal" refers to a portion of an endovascular conduit device that is closer to a user, and the term "distal" refers to a portion that is farther from the user. According to the present disclosure, the term "user" refers to an individual performing any vascular procedure and may include support personnel.

Reference will now be made in detail to exemplary embodiments of the present disclosure, which are illustrated in the accompanying figures. The same reference numbers in different drawings may identify the same or similar elements. In addition, the following detailed description does not limit the present disclosure.

Figure 2:
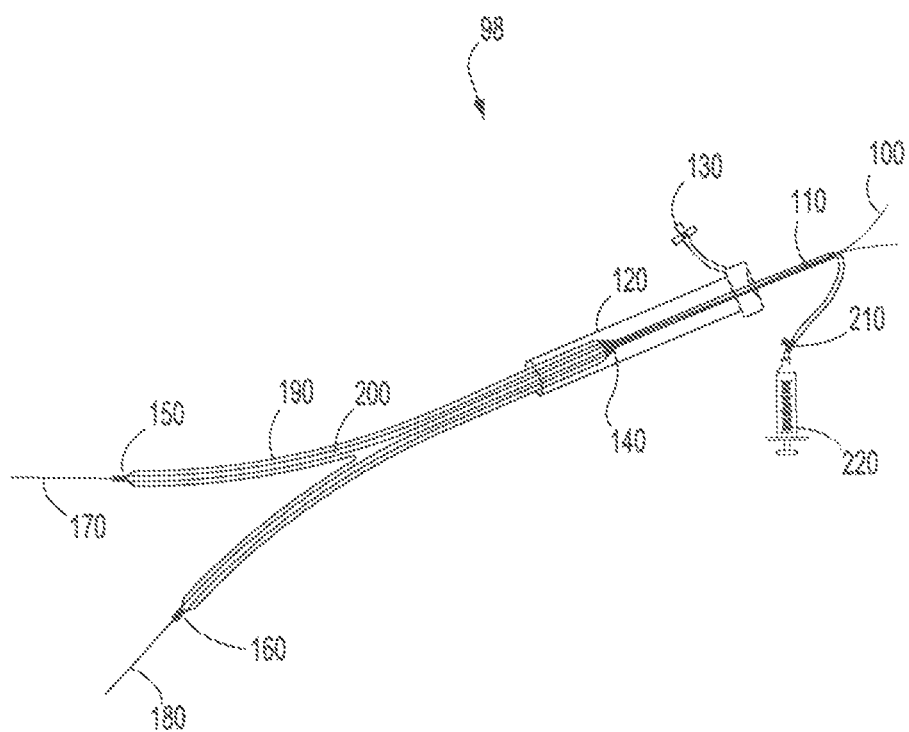
FIG. 2 is a perspective view of an embodiment of an endovascular conduit device, according to the present disclosure.

Referring now to FIG. 2, an embodiment of an endovascular conduit device is presented. Endovascular conduit device 98 is generally comprised of a lumen member 110, an outer-sheath 120, a conduit member 190, and an inflation hub 220. In an embodiment, at least two guide-wires 100 are passed through the proximal portion of lumen member 110 and extend through a first distal guide-wire 170 and a second distal guide-wire 180. Guide-wires 100 may provide rails over which endovascular conduit device 98 may be positioned into a patient's appropriate vessels. In another embodiment, a single guide-wire 100 may be used to conform endovascular conduit device 98 to certain anatomical and technical requirements. In a preferred embodiment, conduit member 190 is passed intravascularly through outer sheath 120.

Lumen member 110 depicts the main shaft of endovascular conduit device 98 to provide stability and push-ability to conduit member 190. Conduit member 190 includes an outer portion 200. Outer-portion 200 may be flexible, sturdy and non-thrombogenic. In an embodiment, lumen member 110 includes an insufflation channel 210 for use with inflation hub 220 to inflate at least one expandable member, such as a proximal expandable member 140, a distal expandable member 150, and a distal expandable member 160. In an embodiment, proximal expandable member 140, distal expandable member 150, and distal expandable member 160 include at least one row of sealing or o-shaped rings or flaps. In a preferred embodiment, proximal expandable member 140, distal expandable member 150, and distal expandable member 160 include at least two rows of sealing or o-shaped rings or flaps. Proximal expandable member 140, distal expandable member 150, and distal expandable member 160 may be inflated by the introduction of air or fluid via inflation hub 220. Inflation hub 220 may be, for example, a syringe or an automatic inflation mechanism. In another embodiment, a hemostatic valve 130 is attached to the proximal portion of outer-sheath 120. Conduit member 190 maintains a low-profile in its non-deployed state; however when deployed, conduit member 190 expands and is able to contain blood within its lumen without any extravasation.

Figure 1:
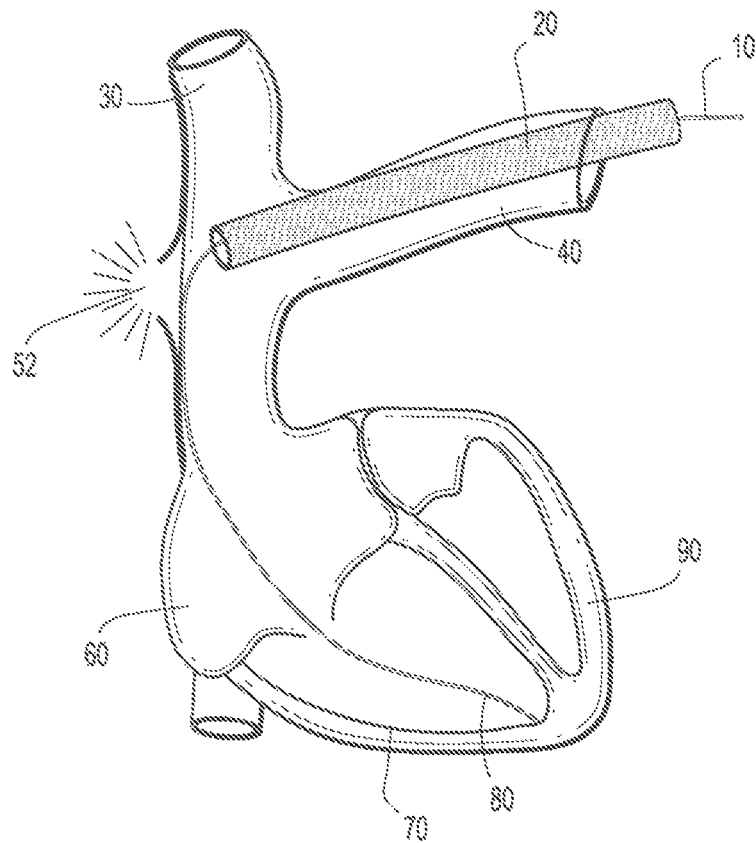
FIG. 1 is a perspective view of a heart and vessels with an implanted cardiac lead, according to the present disclosure.

Referring now to FIGS. 1 and 2, the passage of guide-wires 100 allows endovascular conduit device 98 to be tracked into positioned. In a preferred embodiment, the distal portions of device 98 are split into two segments, one of which is positioned in superior vena cava 30 and the other in right atrium 60. Proximal expandable member 140, distal expandable member 150, and distal expandable member 160 may be inflatable rings or flaps or occlusion members that are controlled by a user from outside the patient's body. Proximal expandable member 140, distal expandable member 150, and distal expandable member 160 are connected to an insufflation channel 210 allows insufflation of air for inflation of proximal expandable member 140, distal expandable member 150, and distal expandable member 160. Proximal expandable member 140, distal expandable member 150, and distal expandable member 160 may be comprised of soft, flexible material that conforms to a vessel wall and provides complete occlusion without leakage outside conduit member 190. In its non-inflated position, endovascular conduit device 98 does not occlude blood flow and does not interfere with lead extraction or other intravascular procedure. Once endovascular conduit device 98 is inflated, blood may be forced into and contained by conduit member 190, thereby preventing blood from entering a torn portion of a blood vessel.

Endovascular conduit device 98 does not require device to vessel wall contact. For this reason, the presence of leads or other objects outside endovascular conduit device 98 do not interfere with the function of endovascular conduit device 98. The functionality of endovascular conduit device 98 allows flexibility in cases of variant anatomy or presence of multiple cardiac leads. For example, in the event of damage to a vessel, endovascular conduit device 98 may be inflated to allow a lead extraction procedure to continue until the lead has been completely removed. At that time, the damaged vessel may be repaired surgically and endovascular conduit device 98 may be removed from the body. Unlike stents and endovascular grafts, endovascular conduit device 98 is only temporarily inserted into a patient's body and removed after a lead extraction surgery is completed.

Figure 3:
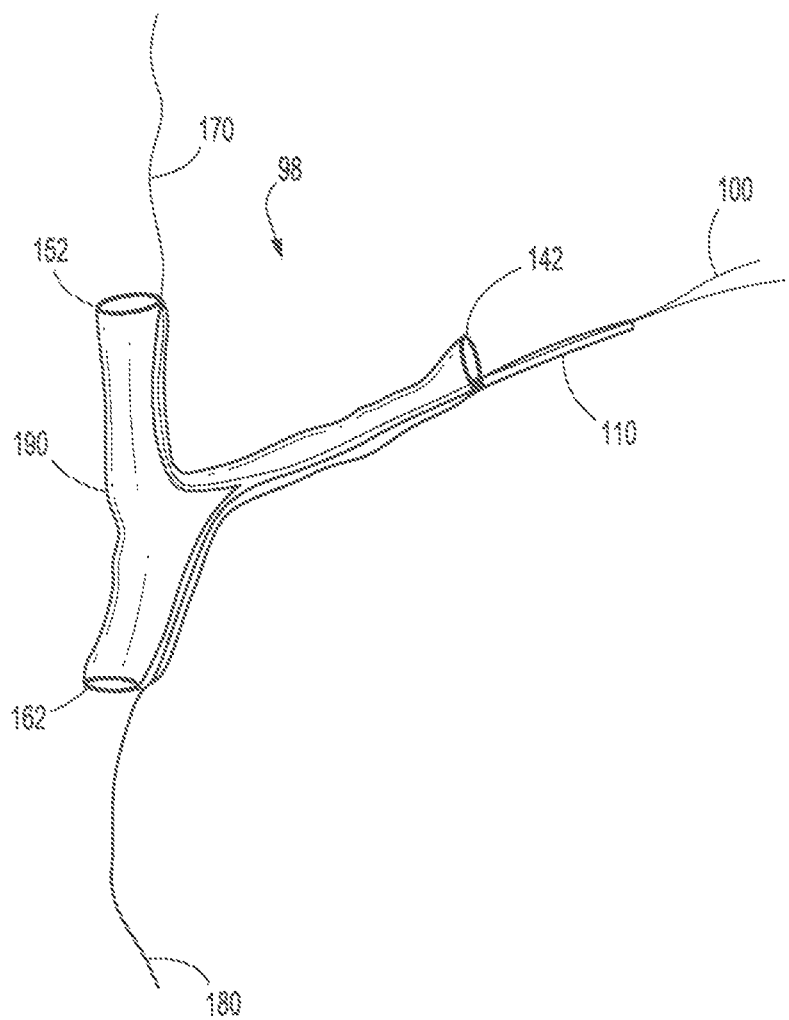
FIG. 3 is a perspective view of an embodiment of an endovascular conduit device, according to the present disclosure.

Referring now to FIG. 3, an endovascular conduit device 98 is presented in a deployed state. Upon inflating a proximal expandable member 142, a distal expandable member 152, and a distal expandable member 162, conduit member 190 expands as blood is forced into its channel. In an expanded state, conduit member 190 is able to contain blood inside its lumen and act as a safe conduit. It is contemplated that conduit member 190 can prevent a catastrophic circulatory collapse when positioned in the right atrium.

Figure 4:
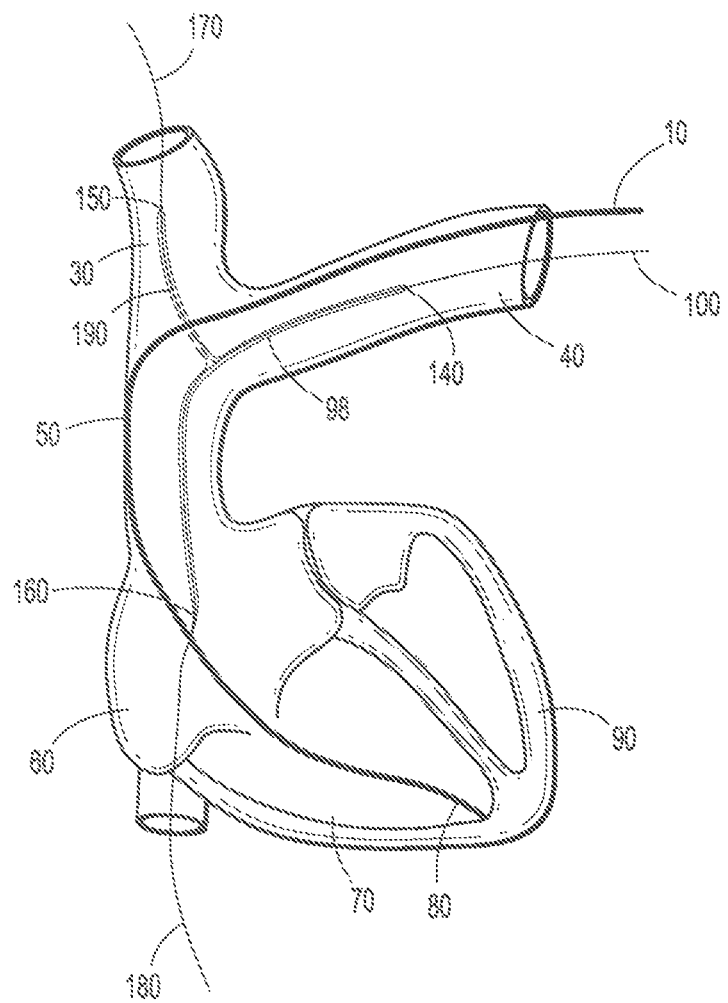
FIG. 4 is a perspective view of a heart and vessels comprising an embodiment of an endovascular conduit device, according to the present disclosure.

Referring now to FIG. 4, a perspective view of a heart and vessels comprising an embodiment of an endovascular conduit device is presented. In a preferred embodiment, endovascular conduit device 98 may be positioned in a patient's intravascular space in a non-deployed state. For example, in a non-deployed state, proximal expandable member 140 is positioned in left innominate vein 40, distal expandable member 150 is positioned in superior-vena cava 30, and distal expandable member 160 is positioned in right atrium 60. A cardiac lead tip is presented at right ventricular apex 80 and adjacent to left ventricle 90.

Referring now to FIGS. 1 through 4, in a method of the present disclosure, conduit member 190 is inserted into outer-sheath 120. Conduit member 190 and lumen member 110 are connected within outer-sheath 120. Proximal expandable member 140 is positioned into left innominate vein 40, distal expandable member 150 is positioned in superior vena cava 30, and distal expandable member 160 is positioned in right atrium 60. At least one guide-wire member 100 is advanced into the proximal portion of lumen member 110 and through distal expandable member 150 and distal expandable member 160. Upon the occurrence of tear 52, the user can introduce an inflation means, such as air, into conduit member 190 through inflation hub 220. In an embodiment, the introduction of an inflation means inflates proximal expandable member 140, distal expandable member 150, and distal expandable member 160 to create a seal and contain fluid within conduit member 190. In another embodiment, the user can independently control the inflation of each expandable member. In yet another embodiment, one of distal expandable member 150 and/or distal expandable member 160 includes an inflation member to control the flow of fluid within conduit member 190. It is contemplated that distal expandable member 160 may also be advanced into a patient's pulmonary artery.

Figure 5:
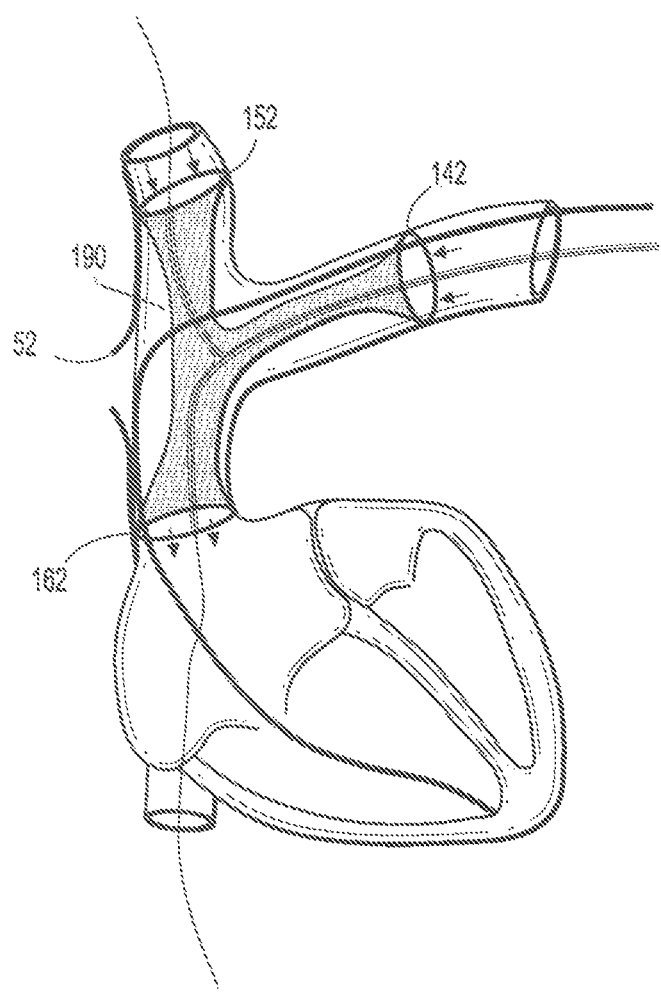
FIG. 5 is a perspective view of a heart and vessels comprising an embodiment of an endovascular conduit device, according to the present disclosure.

Referring now to FIG. 5, proximal expandable member 142, distal expandable member 152, and distal expandable member 162 are inflated to contain blood inside conduit member 190 in the event of tear 52. Upon inflation, blood exits distal member 162 into the right atrium.

Figure 6:
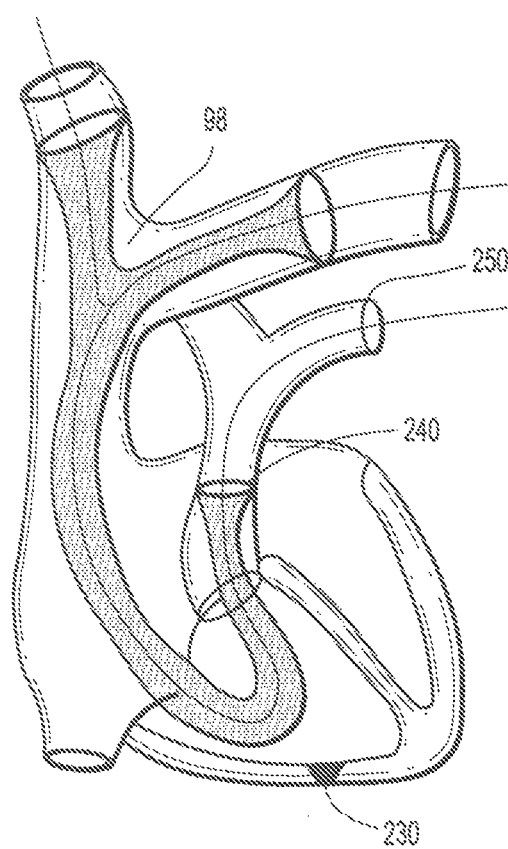
FIG. 6 is a perspective view of a heart and vessels comprising an embodiment of an endovascular conduit device, according to the present disclosure.

Referring now to FIG. 6, a perspective view of a heart and vessels comprising an embodiment of an endovascular conduit device is presented. In an embodiment, a distal portion 240 of endovascular conduit device 98 extends beyond a patient's right atrium to address a tear in the right ventricular apex 230. For example, distal portion 240 may be positioned into a patient's pulmonary artery 250. As a result, endovascular conduit device 98 may direct blood flow beyond a potential tear in the right ventricle directly into pulmonary artery 250.

Figure 7:
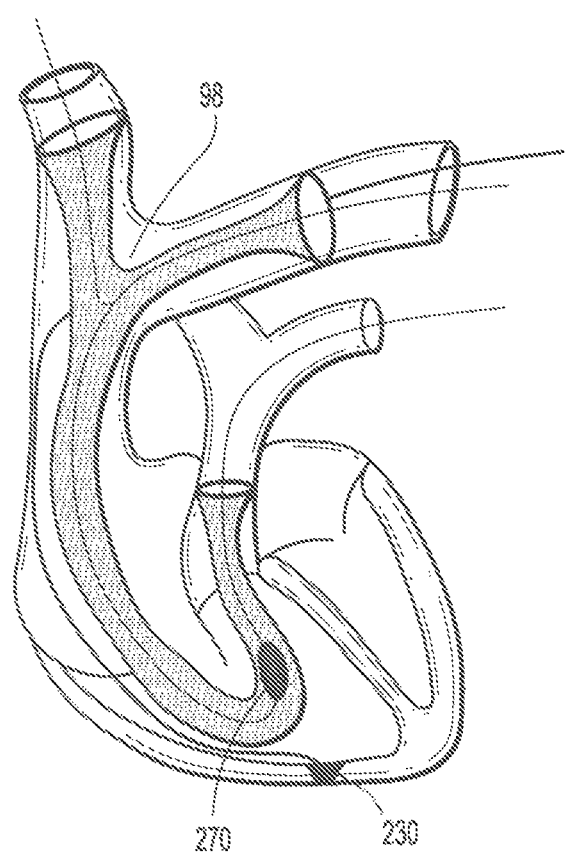
FIG. 7 is a perspective view of a heart and vessels comprising an embodiment of an endovascular conduit device, according to the present disclosure.
Figure 8A:
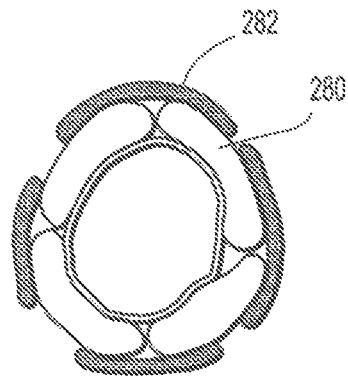
FIG. 8A is a cross-sectional view of an embodiment of an expandable member of an endovascular conduit device, according to the present disclosure.
Figure 8B:
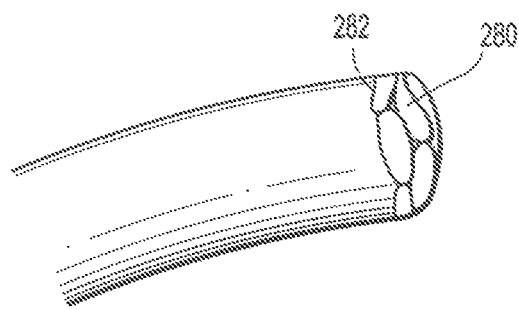
FIG. 8B is a perspective view of an embodiment of an expandable member of an endovascular conduit device, according to the present disclosure.
Figure 8C:
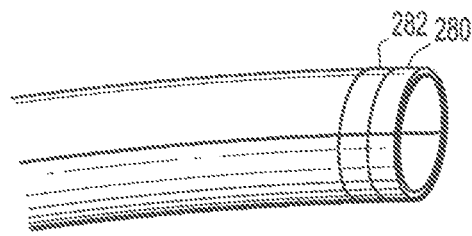
FIG. 8C is a perspective view of an embodiment of an expandable member of an endovascular conduit device, according to the present disclosure.
Figure 8D:
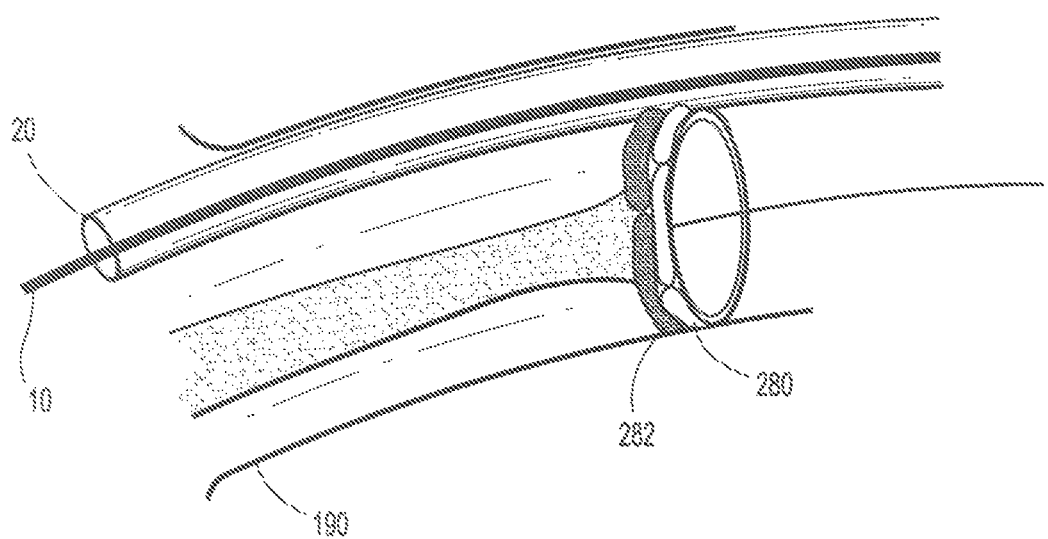
FIG. 8D is a perspective view of an embodiment of an expandable member of an endovascular conduit device, according to the present disclosure.
Figure 8E:
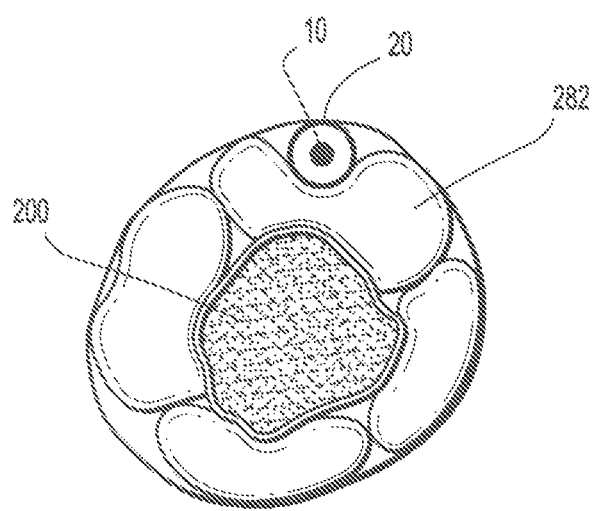
FIG. 8E is a cross-sectional view of an embodiment of an expandable member of an endovascular conduit device, according to the present disclosure.

Referring now to FIG. 7, a perspective view of a heart and vessels comprising yet another embodiment of an endovascular conduit device is presented. In cases where endovascular conduit device 98 is deployed to bypass a tear in right ventricle 230, an inflation member 270 disposed within one distal portion of lumen member 200 may be used to control the flow of fluid within conduit member 200. Inflation member 270 can control the inflation and deflation of conduit member 200 and may increase forward blood flow into a patient's pulmonary arteries. In another embodiment, back flow is prevented by a valve mechanism disposed proximally to inflation member 270.

Referring now to FIGS. 8A through 8E, at least one expandable member of the endovascular conduit device may include at least two rows of sealing or o-shaped expandable members. For example, inner expandable members 280 and outer expandable members 282 may be staggered in the form of two rows within the endovascular conduit device to conform around the shape of a cardiac lead. In a preferred embodiment, outer expandable members 282 conform around the shape of the cardiac lead and inner expandable members 280 offset outer expandable members 282 to provide a secure seal. In this regard, a user could maneuver a medical instrument, such as a catheter, around the exterior portion of the endovascular conduit device during a cardiac lead extraction procedure without compromising a secure seal in the surgical area.

In another embodiment, inner expandable members 280 and outer expandable member 282 have the additional ability to be selectively pressurized. For example, outer expandable members 282, which are in contact with a laser sheath or cardiac leads, may be deflated while inner expandable member 280, which are in contact with a vessel wall, are kept inflated with higher pressure. The ability to selectively pressurize inner expandable members 280 and outer expandable members 282 can allow sheath movement back and forth with relative ease, while maintaining the seal against the vessel wall to prevent leakage of blood.

Figure 9:
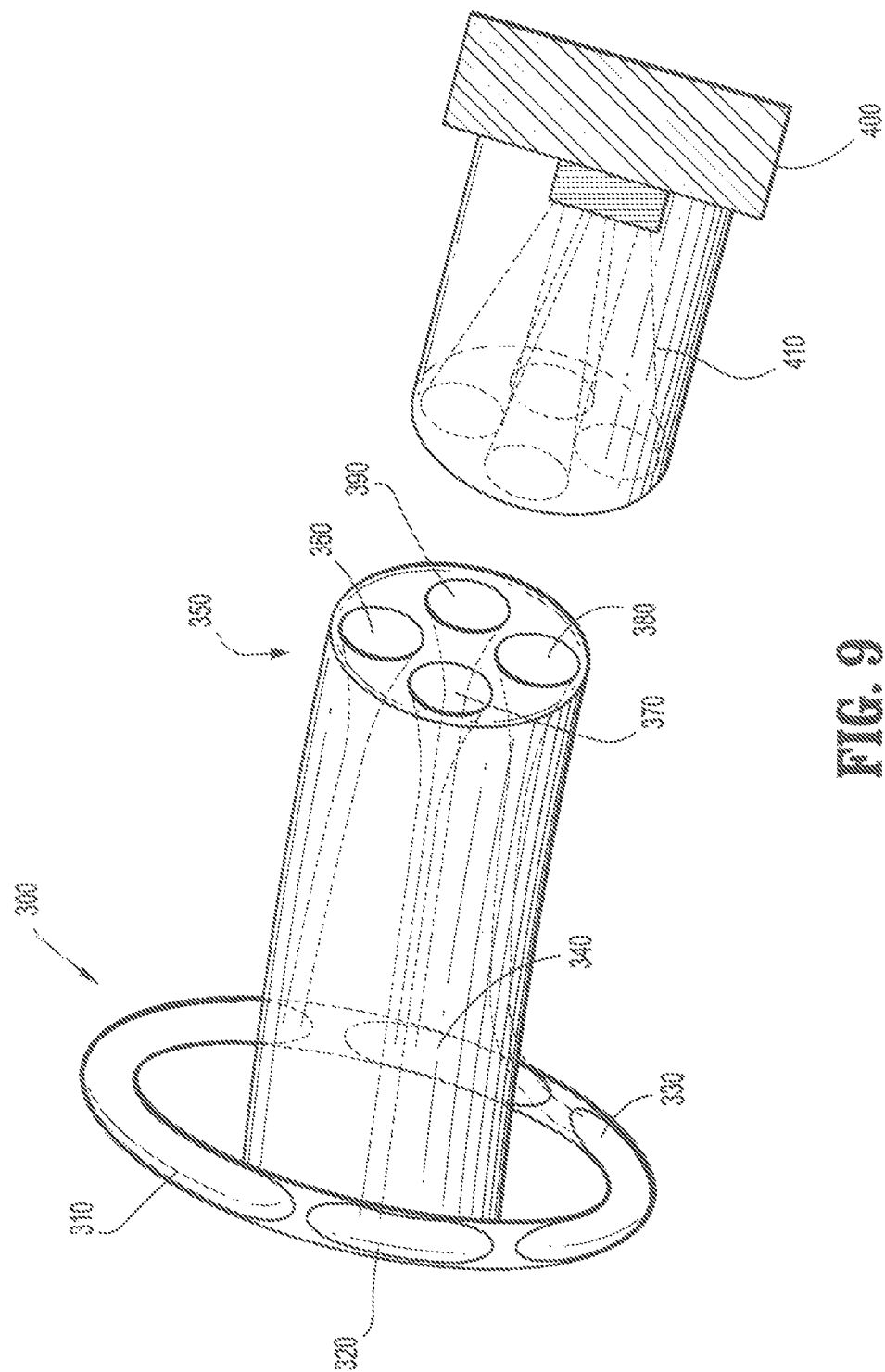
FIG. 9 is a perspective view of an embodiment of an expandable member of an endovascular conduit device, according to the present disclosure.

Referring now to FIG. 9, a perspective view of an embodiment of an expandable member of an endovascular conduit device is presented. In a preferred embodiment, expandable members 300 of the endovascular conduit device are adapted to allow for catheter manipulation. For example, expandable members 310, 320, 330, and 340 may be arranged in two or more separate rows of inflatable lobes. Expandable members 310, 320, 330, and 340 may be individually labeled with fluoroscopic markers so as to allow identification while being deployed using X-rays. Additionally, expandable members 310, 320, 330, and 340 may have individual inflation lumens 350 that correspond to each expandable member. For example, inflation lumen 360 corresponds to expandable member 310, inflation lumen 370 corresponds to expandable member 320, inflation lumen 380 corresponds to expandable member 330, and inflation lumen 390 corresponds to expandable member 340.

In an embodiment, once a user identifies the expandable members 300 which are in direct contact with leads requiring extraction, the user can program inflation hub 400 to inflate each of the expandable members 300 except the ones that are required to be left un-inflated. The ability to selectively inflate the desired expandable members 300 is achieved by regulating the openings of inflation lumens 410 in inflation hub 400. It is contemplated that this feature can allow for continued sheath mobility over leads without trapping the laser or mechanical extraction sheath.

Additionally, at least two or more rows of expandable members 300 may be included to provide additional sealing of blood flow. A second row of expandable members 300 may be preferable given the high degree of variability in lead and blood vessel contact that may vary along the length of a blood vessel. The blood vessel and lead contact also depends upon how many leads are present and if there is rotation or twisting of leads along the length. These considerations can cause marked variations in the shape of a lumen that needs to be occluded by expandable members 300. Therefore, at least one additional row of expandable member 300 may accommodate these variations.

Figure 10:
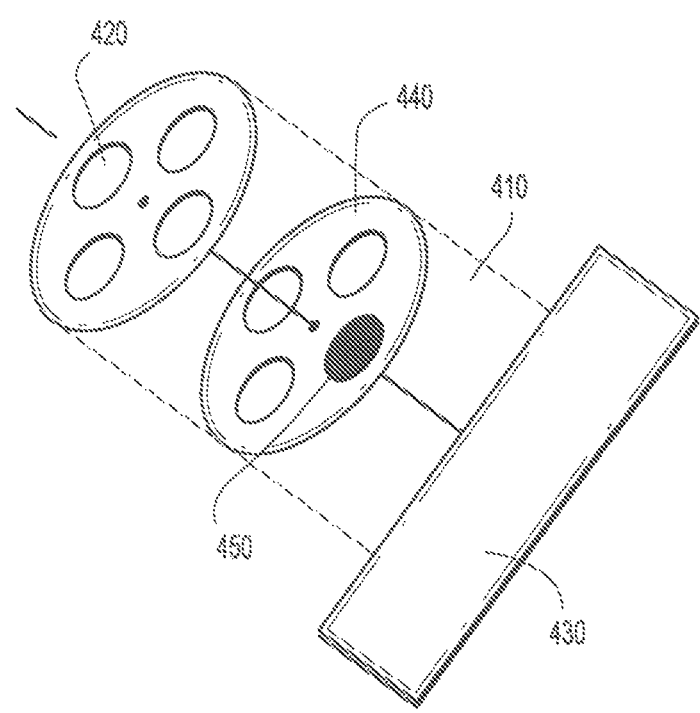
FIG. 10 is a perspective view of an embodiment of an expandable member of an endovascular conduit device, according to the present disclosure.

Referring now to FIG. 10, an inflation channel 410 of the distal portion of endovascular conduit device can include at least one sub-channel 420. Sub-channels 420 may be coupled to an inflation mechanism 430 with at least one rotating disk 440. Rotating disk 440 has at least one opening 450. In an embodiment, one of the openings 450 may be closed so to prevent the entry of air into that particular selected opening.

In another embodiment, it is possible to have more than one rotating disk 440 so that multiple channels 420 can be closed at the same time as desired.

Figure 11:
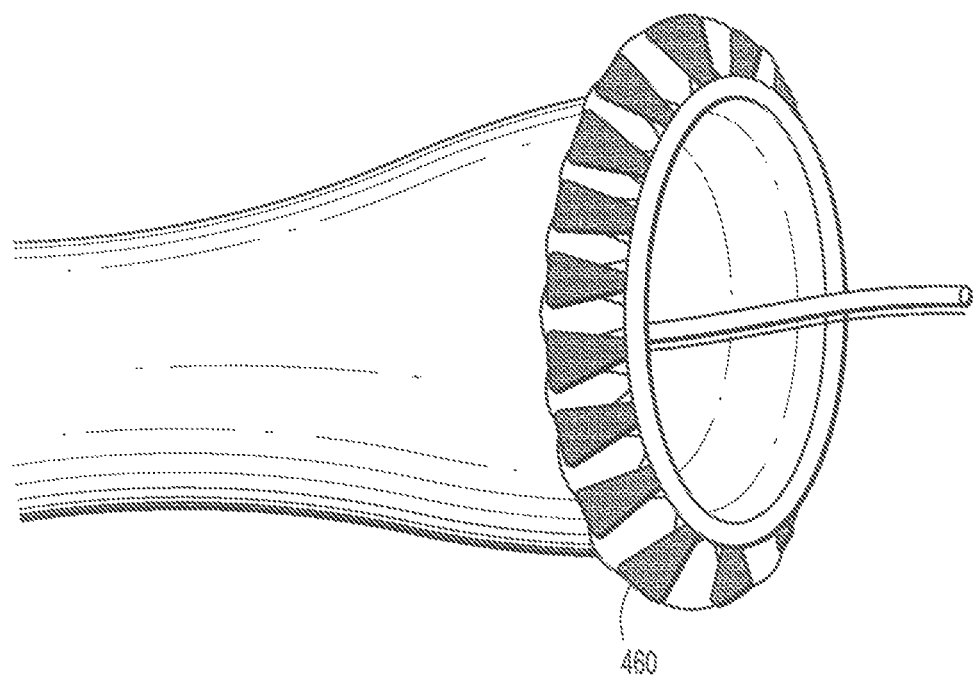
FIG. 11 is a perspective view of an embodiment of an expandable member of an endovascular conduit device, according to the present disclosure.

Referring to FIG. 11, to achieve the function of allowing sealing of blood flow without trapping an extraction tool, a plurality of rubberized flexible members 460 may be used outside the expandable members of endovascular conduit device. Flexible member 460 may be, for example, overlapping flaps that are aligned in two or more rows. It is contemplated that flexible members 460 can adapt to the shape of a lead to provide a complete fluid-tight seal.

Figure 12A:
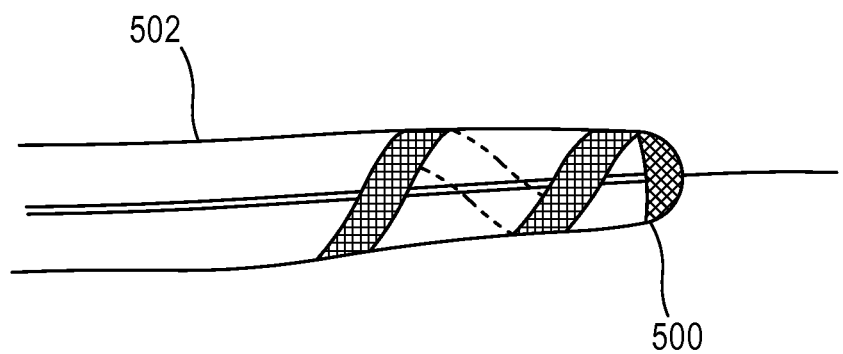
FIG. 12A is a perspective view of an embodiment of an expandable member of an endovascular conduit device, according to the present disclosure.
Figure 12B:
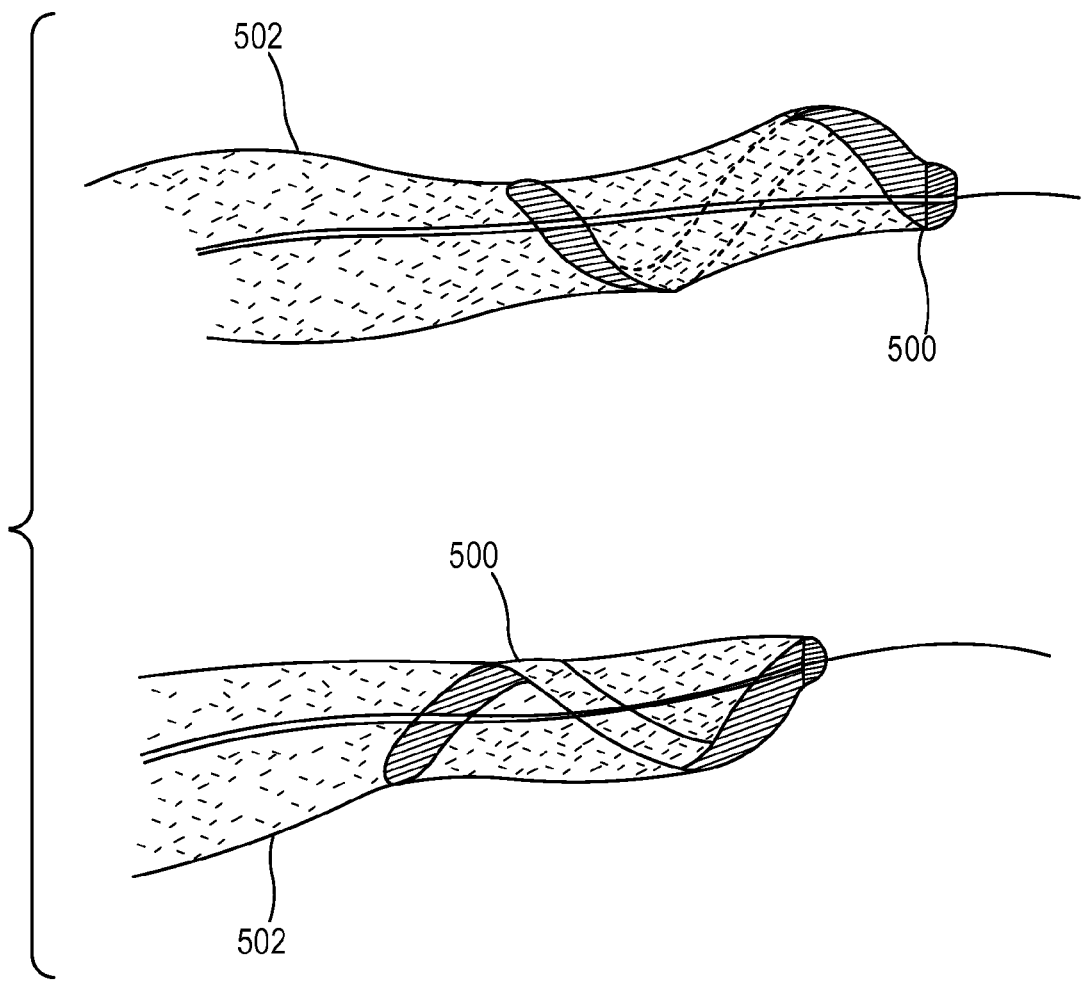
FIG. 12B is a perspective view of an embodiment of an expandable member of an endovascular conduit device, according to the present disclosure.

Referring to FIGS. 12A and 12B, in an embodiment, expandable members 500 may be arranged in a spiral manner around a conduit member 502. The spiral manner feature can make it easier for an endovascular conduit device to be constructed and maintain a low profile in an undeployed state. In an embodiment, expandable members 500 may be constructed with metal that exhibits shape memory, such as, for example, Nitinol®. It is contemplated that no loss of function can occur in a deployed state relative to a circular/spiracle configuration. The spiral arrangement of expandable members 500 can help provide better contact of the endovascular conduit device to a vessel wall in the case of irregularity of the vessel wall.

It is envisioned that the various embodiments of the present disclosure may help increase the safety of cardiac lead extraction procedures by providing patients with a safety net during cardiac lead extraction procedures. In the event a tear occurs within a vessel wall, the present disclosure will help prevent hemodynamic collapse or shock and allow for surgical treatment of the tear in more controlled circumstances.

It is envisioned that present disclosure may be easily and efficiently manufactured and marketed. It is further envisioned that the present disclosure may be made of durable and reliable construction that is susceptible of a low cost of manufacture with regard to both materials and labor, and which accordingly is susceptible of low prices of sale to the consuming public. In addition, it is envisioned that the present disclosure may increase the safety of lead extraction and vascular procedures by providing proximal and distal conduit expandable members that force blood into a safe channel.

It is contemplated that the present disclosure can provide a complete proximal and distal seal with the expandable members so that no leakage occurs outside the conduit member despite variations in anatomy and presence of intravascular leads. It is further contemplated that the present disclosure may be used in all cases of lead extraction, despite any different numbers of leads and variability in where those leads are attached or scarred into a patient's inner vessel wall. In addition, it is contemplated that the present disclosure may provide a mechanism by which circulatory collapse is prevented and surgical repair of a vessel tear may be carried out under controlled circumstances. Furthermore, the present disclosure may provide uninterrupted blood flow whether or not it has to be deployed during a procedure. Moreover, the present disclosure may minimize the risk of clotting of blood that may occur outside the conduit. In addition, the present disclosure is designed to be deployed in the event of a vascular tear, thereby allowing it to remain in a non-inflated, standby mode.

The present disclosure may be used in patients with different vessel diameter. Additionally, the present disclosure may be constructed of flexible but sturdy and non-thrombogenic material or polymer. Furthermore, the present disclosure may be reused in the same patient or another patient if necessary. Moreover, the present disclosure can allow for pulsatile contractions to augment and propel blood flow in the forward direction. It is envisioned that the present disclosure may also be used in gastrointestinal, polypectomy, coronary and carotid artery procedures as well as urological and other invasive procedures that are performed in a body organ cavity. In this manner, the endovascular conduit device may be adapted and used for any body organ where fluid flows from a proximal to a distal end and surgical or catheter intervention is required on the body organ wall.

It will be understood that various modifications may be made to the embodiments disclosed herein. Therefore, the above description should not be construed as limiting, but merely as exemplifications of the various embodiments of the present disclosure. Those skilled in the art will envision other modifications within the scope and spirit of the claims appended hereto.

What is claimed is:

1. An endovascular conduit device comprising:
   an outer-sheath having proximal and distal portions;
   a conduit member partially disposed within the distal portion of the outer-sheath, the conduit member having a proximal portion and at least two distal portions;
   at least one expandable member disposed within the proximal portion and the distal portions and comprising a row of at least four discrete inflatable lobes disposed circumferentially substantially within a circle around the conduit member and adapted to be selectively inflated or left un-inflated and also to conform around a shape of a cardiac lead disposed alongside the device between an exterior of the device and a vessel wall; and
   a lumen member disposed within the conduit member, the lumen member extending proximally from the proximal portion of the outer-sheath through the distal portions of the conduit member.

2. The device of claim 1, wherein the at least one expandable member further comprises individual inflation lumens that correspond to each of the at least four discrete inflatable lobes and the conduit member is comprised of a flexible material to allow for the selective inflation and deflation of individual ones of the at least four discrete inflatable lobes.

3. The device of claim 1, wherein the conduit member is comprised of non-thrombogenic materials.

4. The device of claim 1, wherein the lumen member includes an inflation hub to facilitate the selective inflation and deflation of the individual ones of the at least four discrete inflatable lobes of the at least one expandable member to create a seal and contain fluid within the conduit member.

5. The device of claim 4, wherein the at least one expandable member allows for the maneuverability of at least one medical instrument outside an exterior portion of the lumen member without compromising the seal.

6. The device of claim 4, wherein the inflation hub is disposed proximal to the proximal portion of the lumen member.

7. The device of claim 1, wherein the proximal portion of the outer-sheath includes a control valve to prevent the leakage of air and fluid from entering the conduit member.

8. The device of claim 1, wherein the conduit member includes at least one guide-wire member.

9. The device of claim 8, wherein the at least one guide-wire member extends proximally from the proximal portion of the lumen member through the distal portions of the conduit member.

* * * * *